(12) United States Patent
Slater (10) Patent No.: US 9,566,082 B2
(45) Date of Patent: Feb. 14, 2017

(54) ENDOSCOPIC INSTRUMENT (75) Inventor: Charles R. Slater, Fort Lauderdale, FL (US)

(73) Assignee: Slatr Surgical Holdings LLC, Fort Lauderdale, FL (US)

(*) Notice: Subject to any disclaimer, the term of this patent is extended or adjusted under 35 U.S.C. 154(b) by 1066 days.

(21) Appl. No.: 13/320,670

(22) PCT Filed: May 21, 2010

(86) PCT No.: PCT/US2010/035714
§ 371 (c)(1),
(2), (4) Date: Nov. 15, 2011

(87) PCT Pub. No.: WO2010/135615
PCT Pub. Date: Nov. 25, 2010

(65) Prior Publication Data
US 2012/0065466 A1    Mar. 15, 2012

Related U.S. Application Data

(63) Continuation-in-part of application No. 12/471,041, filed on May 22, 2009, now Pat. No. 8,690,909, and a
(Continued)

(51) Int. Cl.
*A61B 1/00* (2006.01)
*A61B 17/295* (2006.01)
(Continued)

(52) U.S. Cl.
CPC .......... *A61B 17/295* (2013.01); *A61B 17/3201* (2013.01); *A61B 2017/2825* (2013.01); *A61B 2017/2902* (2013.01); *A61B 2017/294* (2013.01); *A61B 2017/2936* (2013.01); *A61B 2017/320064* (2013.01)

(58) Field of Classification Search
CPC .............. A61B 17/3201; A61B 17/295; A61B 2017/2825; A61B 17/28; A61B 17/2804; A61B 17/285; A61B 17/320016; A61B 17/282; A61B 17/29; A61B 2017/2947; A61B 2017/2936; A61B 2017/294; A61B 2017/2926
(Continued)

(56) References Cited

U.S. PATENT DOCUMENTS

2,012,648 A    8/1935 Wheeler
2,172,490 A *  9/1939 Archibald ........................ 74/156
(Continued)

*Primary Examiner* — Gregory Anderson
*Assistant Examiner* — Sarah Simpson
(74) *Attorney, Agent, or Firm* — Gordon & Jacobson, P.C.

(57) ABSTRACT

An endoscopic instrument includes a control wire having a push rod at its distal end and an end effector assembly having first and second effector elements such as scissors blades mounted on a clevis. The effector elements are operated by a cam-pin on the push rod riding in cam-slots defined in the effector elements. According to one aspect of the invention, the effector elements are symmetrically opened even when the push rod is canted relative to the clevis. According to another aspect of the invention, the effector elements can be rotated into a closed configuration that minimizes the distal dimension across the effector elements. In addition, the effector elements, when in the closed configuration, can rotate together to facilitate insertion of the end effector into an entry portion of an endoscope.

10 Claims, 11 Drawing Sheets

Related U.S. Application Data continuation-in-part of application No. 12/471,024, filed on May 22, 2009, now Pat. No. 9,277,932, and a continuation-in-part of application No. 12/471,057, filed on May 22, 2009, now abandoned, and a continuation-in-part of application No. 12/471,066, filed on May 22, 2009, now abandoned.

(51) Int. Cl.
    *A61B 17/3201* (2006.01)
    *A61B 17/28* (2006.01)
    *A61B 17/29* (2006.01)
    *A61B 17/32* (2006.01)

(58) Field of Classification Search
    USPC .................. 606/205, 170, 207; 604/104
    See application file for complete search history.

(56) References Cited

U.S. PATENT DOCUMENTS

| | | |
|---|---|---|
| 2,814,869 A | 12/1957 | Matson |
| 5,203,785 A | 4/1993 | Slater |
| 5,439,471 A | 8/1995 | Kerr |
| 5,439,478 A | 8/1995 | Palmer |
| 5,496,347 A * | 3/1996 | Hashiguchi et al. ......... 606/205 |
| 5,499,992 A | 3/1996 | Meade et al. |
| 5,499,997 A | 3/1996 | Sharpe et al. |
| 5,700,270 A | 12/1997 | Peyser et al. |
| 5,700,276 A | 12/1997 | Benecke |
| 5,716,374 A * | 2/1998 | Francese et al. ............. 606/207 |
| 5,741,285 A | 4/1998 | McBrayer et al. |
| 5,893,874 A | 4/1999 | Bourque et al. |
| 5,904,702 A * | 5/1999 | Ek et al. ....................... 606/206 |
| 5,984,938 A | 11/1999 | Yoon |
| 6,015,412 A | 1/2000 | Mifsud |
| 6,027,522 A | 2/2000 | Palmer |
| 6,059,799 A | 5/2000 | Aranyi et al. |
| 6,159,162 A | 12/2000 | Kostylev et al. |
| 6,206,877 B1 | 3/2001 | Kese et al. |
| 6,409,727 B1 | 6/2002 | Bales et al. |
| 6,554,844 B2 | 4/2003 | Lee et al. |
| 6,634,105 B2 | 10/2003 | Lindermeir |
| 6,773,434 B2 | 8/2004 | Ciarrocca |
| RE39,415 E | 11/2006 | Bales et al. |
| 7,326,229 B2 * | 2/2008 | Dworschak et al. ......... 606/207 |
| 7,572,256 B2 | 8/2009 | Quick |
| 2003/0036679 A1 | 2/2003 | Kortenbach et al. |
| 2003/0236549 A1 | 12/2003 | Bonadio et al. |
| 2005/0101991 A1* | 5/2005 | Ahlberg et al. ............... 606/205 |
| 2005/0192598 A1* | 9/2005 | Johnson et al. ............... 606/148 |
| 2007/0244515 A1 | 10/2007 | Fanous |
| 2010/0198244 A1 | 8/2010 | Spivey et al. |
| 2010/0234866 A1 | 9/2010 | Arcenio et al. |
| 2012/0083784 A1* | 4/2012 | Davison ............. A61B 18/1445 606/48 |

* cited by examiner

ENDOSCOPIC INSTRUMENT

CROSS-REFERENCE TO RELATED APPLICATIONS

This application is a 371 national stage entry application of PCT/US10/35714, with an international filing date of May 21, 2010, which is a continuation-in-part of U.S. Ser. No. 12/471,041, now U.S. Pat. No. 9,690,909, filed May 22, 2009, and is a continuation-in-part of U.S. Ser. No. 12/471,024, filed May 22, 2009, now U.S. Pat. No. 9,277,932, and is a continuation-in-part of U.S. Ser. No. 12/471,057, filed May 22, 2009, now abandoned, and is a continuation-in-part of U.S. Ser. No. 12/471,066, filed May 22, 2009, now abandoned.

BACKGROUND OF THE INVENTION

Field of the Invention

This invention relates broadly to surgical instruments. More particularly, this invention relates to a flexible endoscopic scissors device insertable through a lumen of an endoscope.

State of the Art

Endoscopy is a minimally invasive medical procedure that assesses the interior of the human body using an endoscope. An endoscope generally consists of a rigid or flexible tube, an fiber optic illumination system to guide light provided by a light source through the tube of the endoscope in order to illuminate the organ or object under inspection, and a viewing system for collecting an image of the organ or object under inspection and for recording the image on an internal CCD device (video-endoscope) or for transmitting the image through the tube via a fiber optic bundle to an external video processor for viewing (fiber-endoscope). The endoscope can include one or more "working" channels (typically 2-4 mm in diameter) having a surgeon-accessible entry port through which specialized medical instruments can be passed into the working channels of the endoscope and into the field of view. Such specialized instruments (which can include graspers, biopsy forceps, scissors, etc.) can be used to grasp tissue, sample tissue for biopsy, or separate tissue, all from the inside of the body.

Laparoscopy is a minimally invasive surgical technique in which operations in the abdomen or thorax are performed through small incisions (usually 0.5-1.5 cm) via a rigid or flexible laparoscope. There are generally two types of laparoscopes, including a telescopic rod lens system that is usually connected to a video camera (single chip or three chip) and a digital laparoscope where the camera is placed at the end of the laparoscope, thus eliminating the rod lens system. A fiber optic cable system connected to a light source (halogen or xenon is inserted through a surgical port to illuminate the operative field for viewing. The abdomen is usually insufflated with carbon dioxide gas to create a working and viewing space. Specialized surgical instruments can be introduced into the abdomen or thorax through a surgical port in order to take biopsies and retrieve organs (or pieces thereof) and/or foreign objects from the inside of the body.

The surgical instruments used for endoscopy and laparoscopy generally include end effector means mounted adjacent the distal end of a tube or coil. Handles (or other actuation control means) are mounted to the proximal end of the tube or coil and move an actuator axially through the tube or coil. The distal end of the actuator is mechanically coupled to the end effector means in a manner that transforms the axial movement of the actuator into the desired movement of the end effector means. Such specialized endoscopic and laparoscopic surgical instruments are collectively referred to herein as endoscopic surgical instruments or endoscopic instruments, and endocope(s) and laparoscope(s) and collectively referred to herein as endoscopes. These general principles apply to most endoscopic instruments, but specific endoscopic instruments differ in length, size, stiffness, as well as other characteristics as the instruments are typically designed for a particular application as such instruments can be used for a wide variety of minimally invasive surgical procedures, including the endoscopic and laparoscopic applications summarized above.

SUMMARY OF THE INVENTION

The invention provides an endoscopic instrument having scissors blades and structure adapted to hold tissue from sliding forward along the blades, such structure offset from the cutting edges of the blades.

The invention also provides end effectors with a cam-slot and cam-pin operation and allows the end effectors to rotate together in the same direction when fully closed so as to traverse a non-flexible bend at the entry port of a working channel of an endoscope.

The invention also provides a means for ensuring symmetrical opening of the end effectors about a longitudinal axis extending through a clevis of the instrument.

The invention further provides a push rod and cam-pin construction that does not require extremely high tolerances, and is less costly to manufacture.

The invention additionally provides a high degree of accurate rotational manipulation of the end effector about the longitudinal axis of the device in a manner so that the end effector can be rotated even within a retroflexed endoscope.

According to the invention, an endoscopic instrument includes an elongate flexible tubular member having a proximal end and a distal end, a clevis at the distal end of the tubular member, and an end effector having first and second elements, such as scissors blades or grasping jaws, pivotally mounted on an axle on the clevis. A control member is axially movable through the tubular member, and a distal end of the control member is provided with a push rod that is coupled to the end effector elements to effect relative movement of the elements in an opposing opening and closing action as the control member is longitudinally translated back and forth within the tubular member. A proximal handle assembly is coupled to the proximal ends of the tubular member and the control member to permit longitudinal movement of the control member within the tubular member, and optionally rotation of the control member relative to the tubular member, as discussed further below.

According to one aspect of the invention, laterally offset from the cutting edges at least one of the blades of an endoscopic scissors, and preferably both of the blades, includes a friction enhancing tissue stop that functions to hold and/or put traction on tissue previous to, or while, cutting the tissue. In one embodiment, the tissue stop includes at least one set of tenaculum or grasping needle points provided at the distal end of the blade and/or as well as a position intermediate the proximal and distal ends. In another embodiment, the tissue stop includes a row of saw-like projections mounted adjacent (or "with close proximity") to the cutting edge of the blades. Each tissue stop is a distinct structure from the blade provided as a separate component on or within the ground or lateral surface of the scissor blade, and are mechanically bonded thereat.

In a second aspect of the invention the proximal end of preferably each end effector element and the distal end of the control member are coupled together in a cam-pin and cam-slot assembly. The distal end of the control member includes a push rod provided with a cam-pin. The cam-pin rides in a cam-slot in the proximal end of each element. As the control member is translated, the cam-pin rides in the cam-slots causing the end effector elements to collectively move in an opposing opening and closing action. Relative proximal movement of the control member thus causes the end effector elements to move into a closed configuration. According to this aspect of the invention, the proximal end of the cam-slot includes a bilaterally widened area (on both sides of the longitudinal axis of the cam-slot so that when the pin is fully retracted into the bilaterally widened area the end effector elements are now free to rotate together in the same direction. This effectively shortens the rigid non-bendable length of the end effector allowing for insertion of a longer-than-usual end effector which previously would not have been passable into and through the entry portion of the endoscope. In addition, several constructions and configurations of the push rod with cam-pin are provided that have an advantage in that they do not require the same tolerances for assembly as prior art push rod with cam-pin constructions and are less costly to manufacture. Further, a guide is provided at the distal end of the push rod to cause the end effector elements to open symmetrically about the longitudinal axis through the clevis, even when the push rod is canted relative to that longitudinal axis.

According to another aspect of the invention, the end effector of the endoscopic instrument is rotatable about the axis of the tubular member by rotation of the control member, as actuated from the proximal handle. According to another aspect of the invention, to permit such rotation, the distal end of the tubular member is provided with a stationary inner bearing, and the clevis for the end effectors is rotatably secured to an outer bearing that rotates on the inner bearing. The torque applied to the control member is transferred to the push rod and cam-pin at the distal end thereof. As a result of the applied torque, the end effectors and clevis smoothly rotate at the interface of the inner and outer bearings.

According to yet another aspect of the invention, the control member has decreasing torsional and flexural stiffness from the proximal towards the distal portions of its length. The control member is preferably constructed of a proximal portion and a distal portion and a coupling element that mechanically joins the proximal and distal portions. The proximal portion is a composite carbon rod or a spring steel stainless wire. The distal portion is a thin multi-strand, drawn brazed strand cable or a single superelastic metal wire. The distal portion is capable of offering significant resilient flexibility, as well as accurate and directionally even application of torque—both clockwise and counterclockwise—without causing jump or whip (uneven or sudden rotation). The coupling element is preferably a portion of hypotube provided at the adjacent ends of the proximal and distal portions, although it may include other devices or methods as well as threading, welding, etc.

Additional advantages of the invention will become apparent to those skilled in the art upon reference to the detailed description taken in conjunction with the provided figures.

BRIEF DESCRIPTION OF THE DRAWINGS

PRIOR ART

DETAILED DESCRIPTION OF THE PREFERRED EMBODIMENTS

Turning now to FIGS. 1 through 4, an endoscopic instrument 10 according to the invention is shown. The endoscopic instrument 10 includes an elongate tubular member 12 preferably of a flexible construction having a proximal end 14 and a distal end 16, a clevis 18 rotatably mounted at the distal end 16 of the tubular member 12, and an end effector assembly 20 dimensioned for passage within the working channel of an endoscope. A control member 28 is axially displaceable through and rotatable within the tubular member 12. The distal end 30 of the control member 28 is provided with a push rod 32 that is coupled to the end effector 20 to effect relative movement of the end effector in an opening and closing action, e.g., scissoring action, as the control member 28 is longitudinally translated within the tubular member 12, as discussed in more detail below. A proximal handle assembly 34 is coupled to the proximal end 14 of the tubular member 12 and the proximal end 36 of the control member 28 to effect relative longitudinal and rotational movement of the control member 28 and the tubular member 12, as discussed further below.

Figure 1:
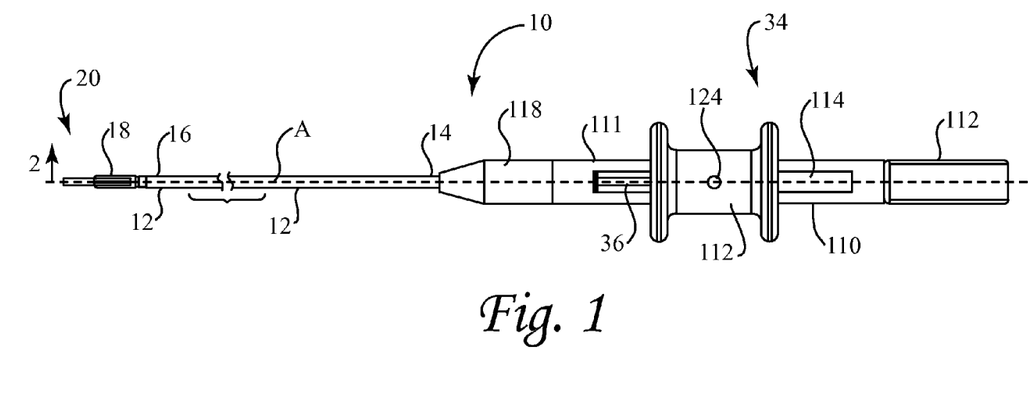
FIG. 1 is a side elevation view of an endoscopic instrument according to the invention.
Figure 2:
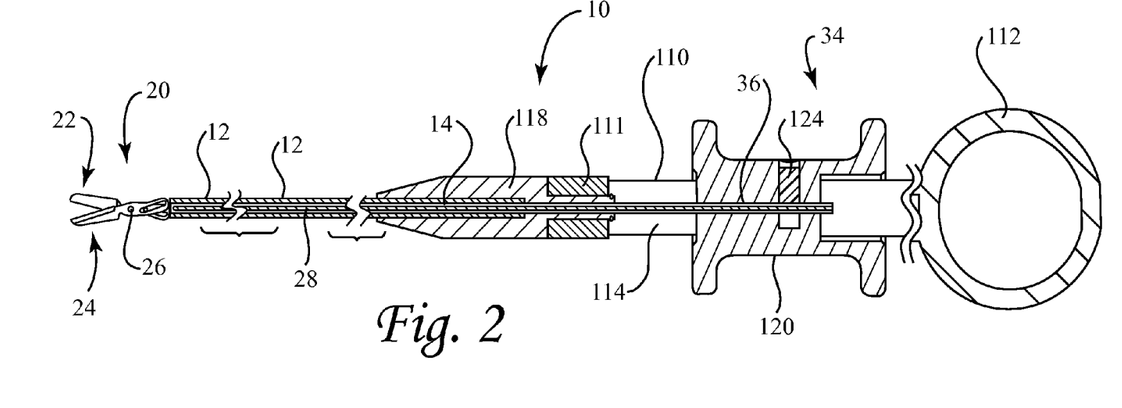
FIG. 2 is a longitudinal section of the endoscopic instrument of FIG. 1 taken along line 2-2 in FIG. 1.
Figure 3:
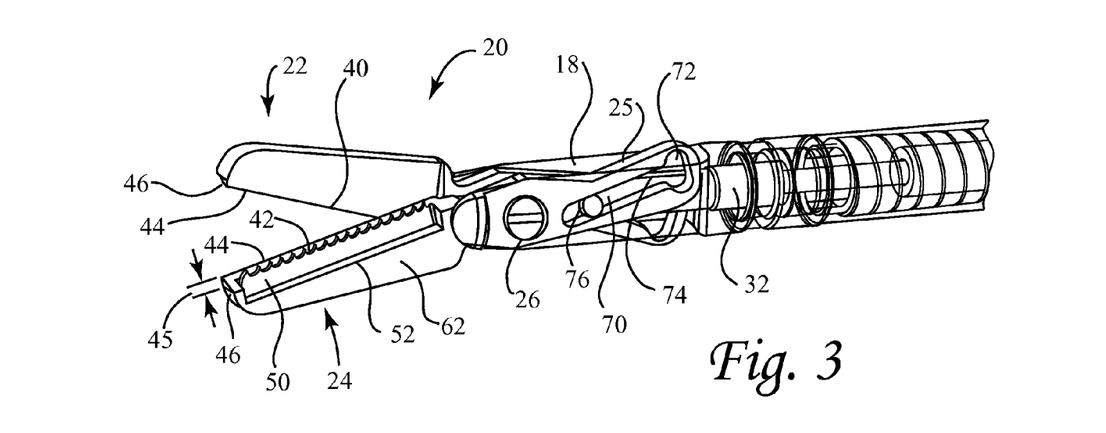
FIG. 3 is a partially transparent isometric view of the distal end of the endoscopic instrument of FIG. 1.
Figure 4:
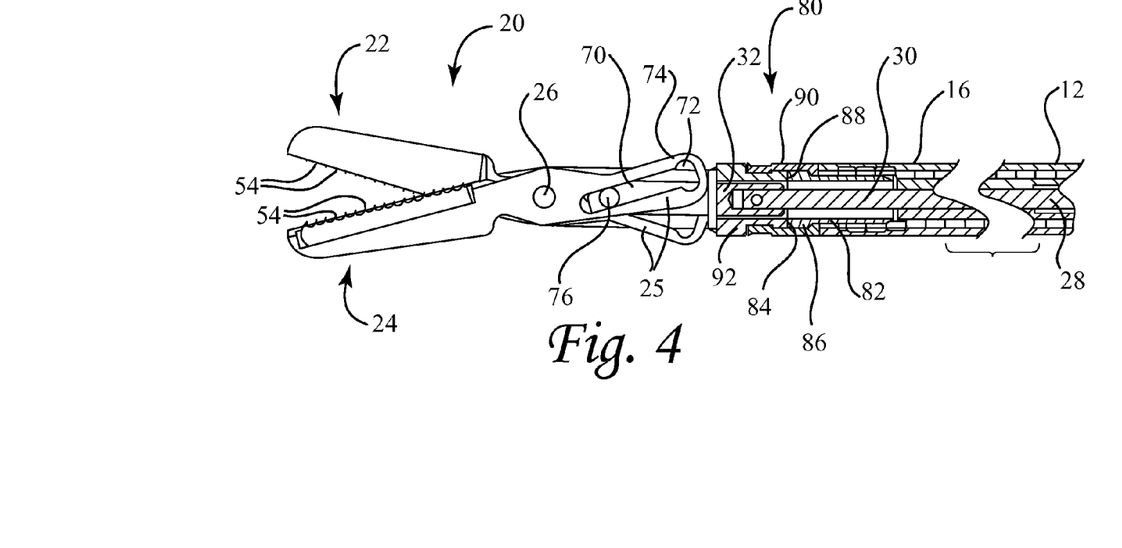
FIG. 4 is a broken partial section view of the distal end of the endoscopic instrument of FIG. 1.

Referring to FIGS. 3 and 4, in the embodiment shown, the end effector assembly 20 is a scissors assembly including scissors blades 22, 24 pivotally mounted on an axle 26 at the clevis 18. The blades 22, 24 each include a medial surface 40, a ground (or honed) surface 42, which extends to, and ends in a sharp cutting edge 44 at an intersection with the medial surface, and a lateral surface 62 opposite the medial surface. The cutting edge 44 extends from a location distal the pivot point to the distal end 46 of the blade.

According to one aspect of the invention, preferably at least one blade, and more preferably both blades, includes a friction enhancing tissue stop 50 that is laterally offset by an offset 45 from the cutting edge 44 (so as not to be present at the cutting edge at all). The offset 45 is preferably less than 0.25 mm (0.012 inch) but may be a full blade-thickness offset from the cutting edge such that the tissue stop is mechanically attached to the lateral surface 62. The tissue stop 50 functions to hold and/or put fraction on tissue without cutting the biological tissue, to hold or put traction on non-metallic articles such as sutures without cutting the same, and to not interfere with the cutting edge 44 of the blade. It is advantageous that at least a portion of the tissue stop can be provided proximal to the distal end 46 of the scissors blade to stably retain tissue and prevent its advancement down the ground surface 42 to the distal end 46 of the blade. Each tissue stop 50 may be provided as an insert within a respective recess 52 that extends within the lateral side 62 of the respective blades 22, 24. Each tissue stop 50 is retained in its recess 52 preferably by welding, bonding, brazing, riveting or another mechanical bonding or fit. Optionally, the tissue stops 50 may be manufactured from a different material than the material or materials defining the blades 22, 24. By way of example only, while the blades 22, 24 are preferably constructed of metal, the tissue stops 50 may be constructed of the same metal, a different metal, a carbon composite or a polymer composite. The tissue stops may be readily shaped by molding, casting, machining, photo-etching, forming or stamping.

Figures 5, 6, 7, 8:
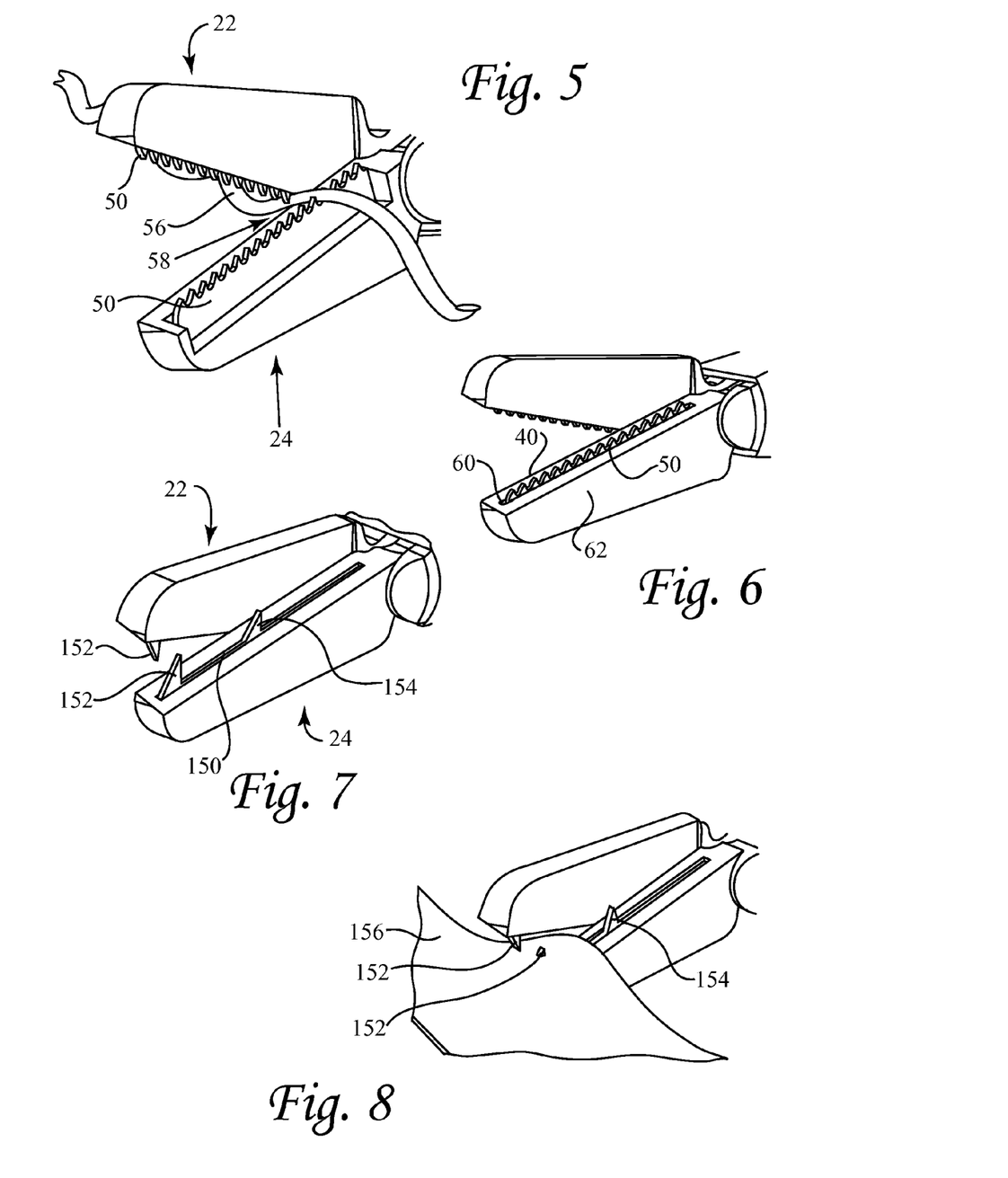
FIG. 5 is an isometric view of endoscopic scissors blades with a first embodiment of tissue stops coupled to the blades of the endoscopic instrument and showing the use of the tissue stops to retain a blood vessel.
FIG. 6 is an isometric view of endoscopic scissors blades with a second embodiment of tissue stops coupled to the blades of the endoscopic instrument.
FIG. 7 is an isometric view of endoscopic scissors blades with a third embodiment of tissue stops coupled to the blades of the endoscopic instrument.
FIG. 8 illustrates the use of the tissue stops of FIG. 7 to engage tissue.

By way of example, in the embodiment shown in FIGS. 3 through 5, the tissue stops 50 are provided on both of the scissors blades 22, 24 and include a continuous row of saw-like toothed projections 54. The projections are not of sufficient height above the cutting edge 44 or sharpness to cut through tissue. The projections function to assist in holding slippery tissue, including blood vessels such as artery 56 in place even in the rear-most position of the open scissors blades 22, 24, e.g., at 58, and prevent the common occurrence of such tissue from sliding forward and out from between the blades as the blades are moved into a closed configuration. Turning to FIG. 6, the tissue stops 50 may alternatively be received within a slot 60 in the ground surface 42 (with both the medial side 40 and lateral side 62 of the blade enclosing portions of the stop). The stop functions in the same manner as described above. As yet another alternative, the tissue stops 50 may be mounted external the blade on the lateral side 62.

Referring now to FIG. 7, another embodiment of a tissue stop 150 is shown in combination with each scissors blade 22, 24. Each tissue stop 150 includes a first tenaculum (or grasping needle point) 152 provided adjacent, but proximally displaced relative to the distal end of its respective blade (e.g., blade 24), as well as a second tenaculum 154 at a position intermediate the proximal and distal ends of the blade. In each stop 150, the distal tenaculum 152 preferably extends a greater height from the ground surface 42 and is larger than the more proximal tenaculum 154. As shown in FIG. 8, the distal tenaculum 152 is readily adapted to effectively pierce and maneuver tissue 154, whereas the more proximal tenaculum 154 is configured to prevent tissue from sliding down the ground surface 42 toward the distal end 46 of the blade 24.

Figure 9:
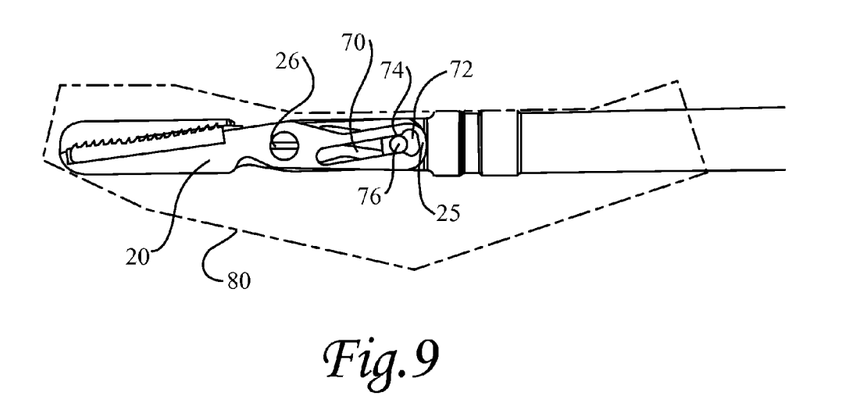
FIGS. 9 and 10 are schematic illustrations of the operation of the cam-pin and cam-slot arrangement of the endoscopic instrument.
Figure 10:
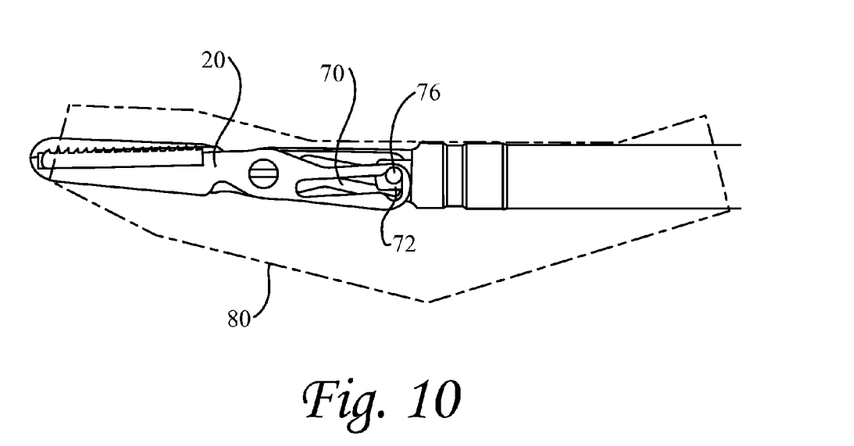
Figure 11:
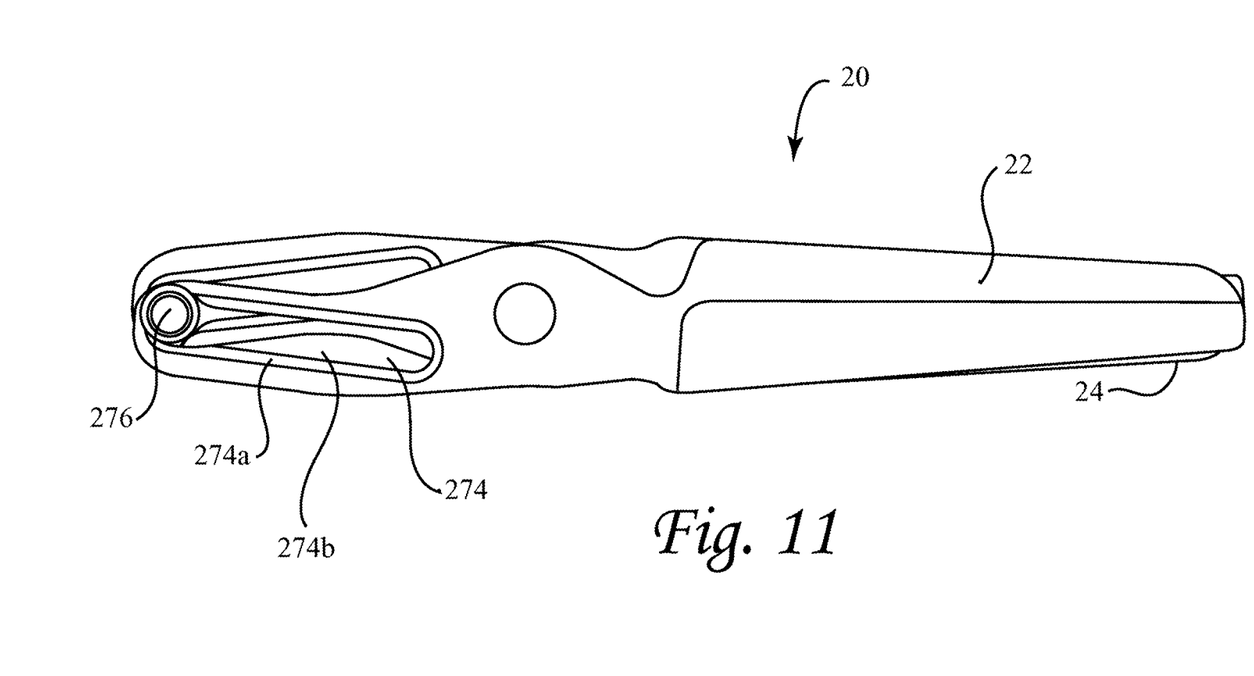
FIG. 11 is a schematic illustration of an end effector provided with an alternate embodiment of a cam-pin and cam-slot arrangement.
Figure 12:
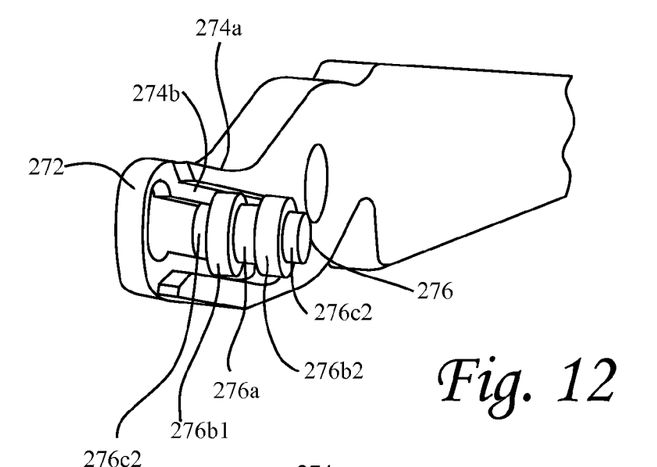
FIGS. 12-14 are partially transparent perspective views of the embodiment shown in FIG. 11.

Referring back to FIGS. 3 and 4, the blade end effector elements 22, 24 of the end effector assembly 20 are moved between open and closed configurations via a cam-pin and cam-slot assembly. More specifically, the tang 25 at the proximal end of each blade 22, 24 (proximal of the axle 26) includes a longitudinally extending cam-slot 70 (shown best with respect to blade 24) that is oriented at an oblique angle relative to the longitudinal axis A of the tubular member 12. The cam-slot 70 includes a bilaterally widened area 72 (on both sides of the axis of the cam-slot), preferably located at the proximalmost end 74 of the cam-slot. The push rod 32 joined to the distal end 30 of the control member 28 includes and is provided with a transverse cam-pin 76 that rides in the cam-slot 70 of each of the blades 22, 24. The assembly of the cam-pin 76 to the push rod 32 is discussed in detail below. As the control member 28 is translated within the tubular member 12 by operation of the proximal handle assembly 34, the cam-pin 76 is caused to ride within the cam-slots 70 causing the blades 22, 24 to move in a scissoring action, with relative proximal movement of the control member causing the blades to move into a closed configuration, as shown in FIG. 9. In the closed configuration shown in FIG. 9 the scissors blades are rigidly held by the tolerances of the cam-pin and cam-slot arrangement to define a stiff 'non-giving' assembly about the clevis 18 (FIG. 3). This can present difficulty in maneuvering the end effector assembly, particularly where longer scissors blades or other longer end effectors are used, through the relatively rigid and bent entry port 80 (shown in broken lines) of a working channel of an endoscope. However, as shown in FIG. 10, when the cam-pin is further retracted into the bilaterally widened area 72 at the proximal end 74 of the cam-slot 70, sufficient room is provided for the cam-pin 76 to permit the blades 22, 24 of the end effector assembly 20 to rotate together in the same direction about the longitudinal axis A of the instrument. This effectively shortens the rigid non-bendable length of the end effector assembly 20 allowing for passage of a longer end effector assembly 20 into the entry portion 80 of a working channel of an endoscope. As such, as shown in FIG. 10, a longer rigid end effector 20 operated by a cam-pin and cam-slot arrangement can be used.

In FIGS. 9 and 10, the proximal end of the tang 25 is required to have a proximally widened area to accommodate the bilaterally widened area 72 of the slot formed therein. This results in the proximal end of the end effector 20 having a relatively wide width which can extend out of the clevis when the end effector is in the fully closed configuration. This portion of the end effector could interfere with a protective sheath extending over the clevis or with the entry port of the endoscope.

Figure 13:
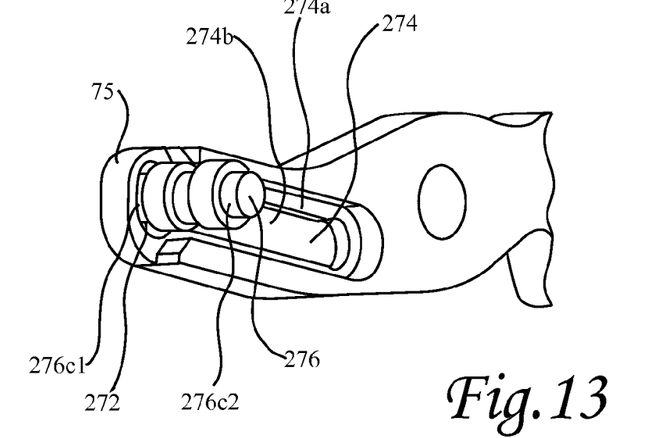
Figure 14:
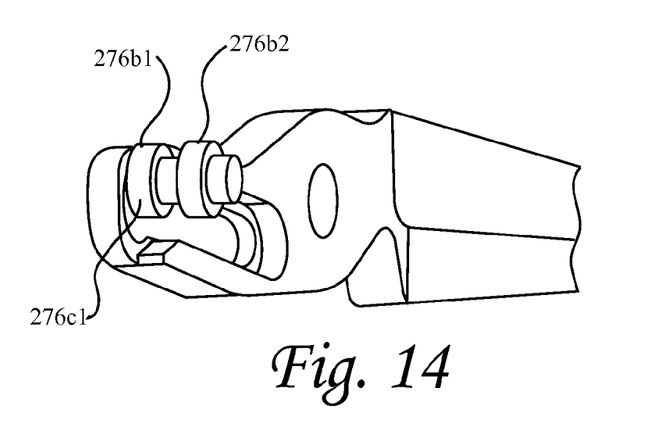

Referring now to FIGS. 11 through 14, another embodiment of a cam-pin and cam-slot arrangement is shown. The cam-slot 274 is stepped so as to define a wider medial slot portion 274a and a narrower lateral slot portion 274b (smaller than cam-slot 74 in FIGS. 3, 4 and 9). Medial and lateral are defined relative to a longitudinal axis of the instrument, with medial being closer to the longitudinal axis and lateral being further from the longitudinal axis, and within the plane through which the end effectors move between open and closed configurations. Lateral slot portion 276a includes a widened proximal slot 272a, with width being measured parallel to the plane through which the end effectors move between open and closed configurations. Medial slot portion 274b is open at and proximal of the widened proximal slot 272a. The cam-pin 276 also has as stepped diameter, having a central portion 276a at which it is coupled to the push rod 232, first diameter medial portions 274a1, 274a2 adjacent to and on either side of the central portion 276a, and smaller second diameter lateral portions 276c1, 276c2 adjacent to and on either side of the medial portions 274a1, 274a2. In most of the travel of the cam-pin 276 within cam-slot 274, each medial portion 274a1, 274a2 is sized to ride closely within a medial slot portion 272a of a respective end effector element, and each lateral portion 276c1, 276c2 is sized to ride closely within a lateral slot portion 274b. Referring to FIG. 13, when the end effector is in the fully closed configuration, both the medial and lateral portions of the cam-pin 276 travel to the widened slot area 272a of the cam-slot 274 at the back end of the end effector elements. The smaller diameter lateral portions 276c1, 276c2 of the cam-pin 276 are constrained within the confines of the widened area 272 of the cam-slot 274, while the larger diameter medial portions 276b1, 276b2 enter 'air' and are free of the medial slot portion 274a. Referring to FIG. 14, the medial portions 276b1, 276b2 can travel back further over the tang, straddling the back end of the tang 75. This provides the slop that allows the end effector elements 22, 24 to rotate together when in a closed configuration (for insertion into an entry portion of an endoscope), reduces the proximal dimension across the end effector 20 when in a closed configuration, and permits the end effector elements 22, 24 to close together by a relatively greater rotational degree (than in the embodiment shown in FIGS. 9 and 10) to reduce the distal dimension of the end effector 20 in the closed configuration.

Figure 15:
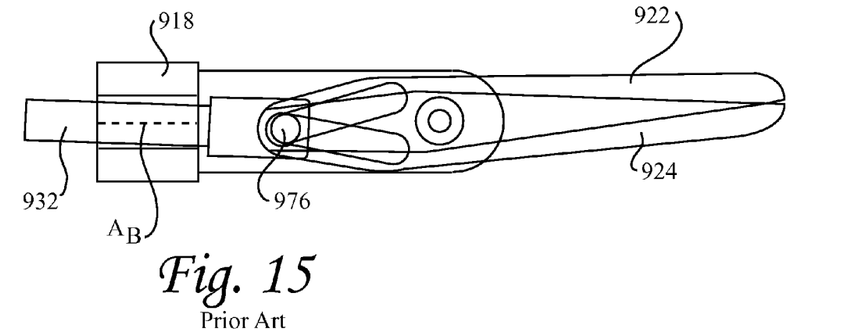
FIGS. 15 through 17 are schematic illustrations of a prior art cam-pin and cam-slot operated scissors end effector.
Figure 16:
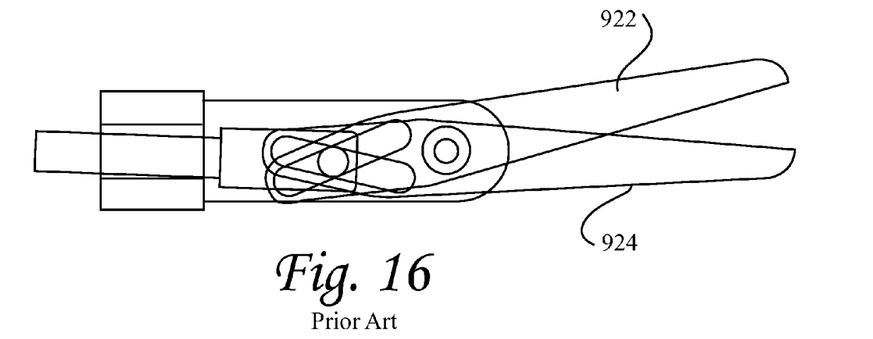
Figure 17:
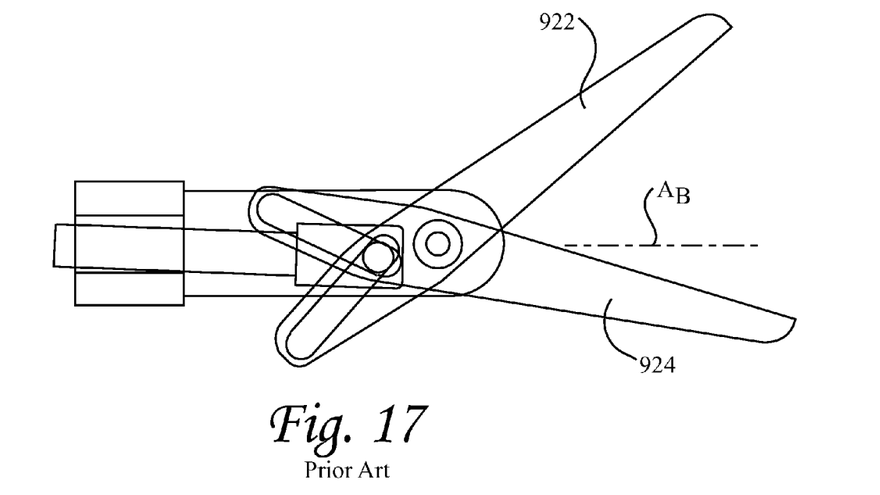

Referring to PRIOR ART FIGS. 15 through 17, it is recognized that the when advancing a push rod 932 relative to the clevis 918 to move the end effectors 922, 924 from a closed configuration (FIG. 15) to the open configuration (FIG. 17), sufficient room is provided within the bore of the clevis 918 to allow the push rod 932 to move off a concentric position relative to the bore axis $A_B$ and result in canting of the push rod 932. With even slight canting of the push rod 932, the cam-pin 976 is moved into an off-center location in its travel. This misalignment causes the end effectors 922, 924 to be rotated in an asymmetric angular alignment relative to the bore axis $A_B$ as they are moved into the open configuration (FIG. 17). This results in reduced precision control of the instrument and operator difficulty in engaging and operating on the target tissue.

Figure 18:
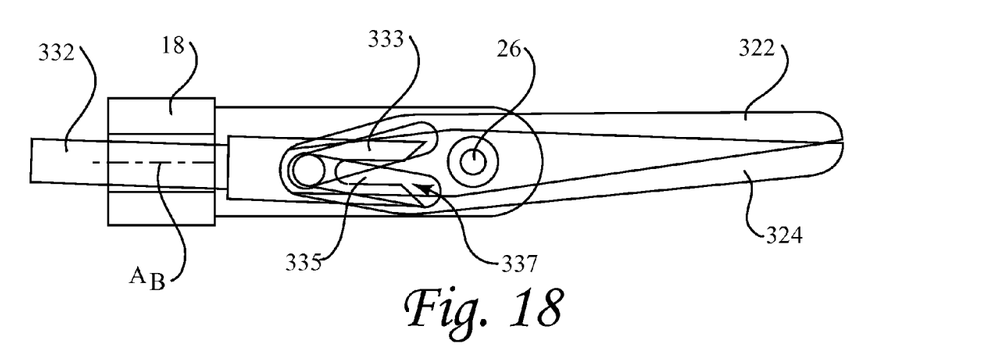
FIGS. 18 through 20 are schematic illustrations of an end effector provided with a guiding push rod according to one aspect of the endoscopic instrument of the invention.
Figure 19:
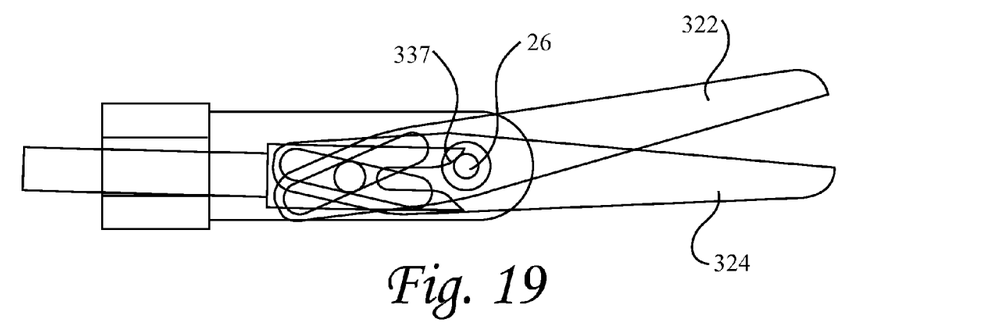
Figure 20:
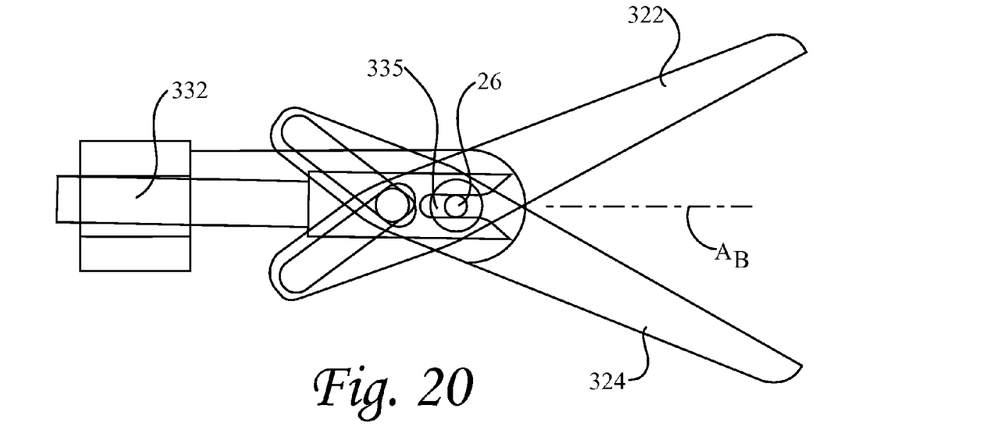

Turning now to FIGS. 18 through 20, in order to eliminate asymmetrical opening of the end effectors 320, 322 about the bore axis $A_B$, the distal end of the push rod 332 is formed with or otherwise coupled to an alignment guide 333. The alignment guide 333 includes a longitudinal slot 335 with a flared opening 337. As the guide is advanced relative to the end effectors in order to move the end effectors into a closed configuration, the flared opening 337 of the guide rides against the axle 26 (FIG. 19). As the push rod is further advanced, the axle 26 is constrained to travel within the slot 335 and ensure symmetrical opening of the end effectors 320, 322 even when the push rod is canted relative to the bore axis $A_B$ (FIG. 20). While the figures illustrate this concept in conjunction with a conventional scissors end effector, this aspect of the invention also may be used with any of the end effectors referenced herein.

Figure 21:
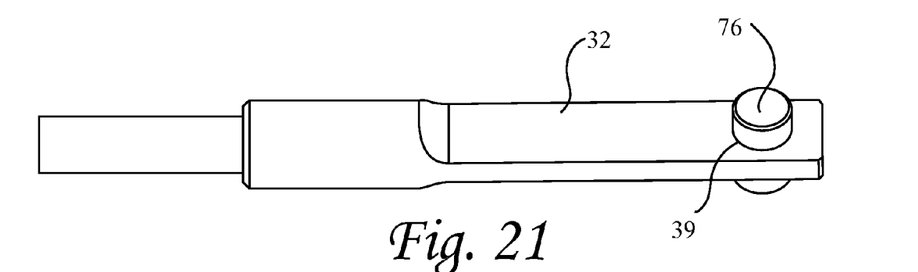
FIG. 21 is a longitudinal perspective view of one push rod cam-pin assembly for use in the endoscopic instrument.

The cam-pin for the embodiment shown in FIGS. 3 and 4 may be coupled to the push rod in any conventional manner. Referring to FIG. 21, one conventional manner provides for machining both the push rod 32 and cam-pin 76 and mating the two together in a force fit. This requires very tight dimensional tolerances between the outer diameter of the cam-pin 76 and the inner diameter of the transverse hole 39 through the push rod. One manner of making the parts requires CNC machining which results in a relatively high cost of construction. Moreover, using this design and manufacture, if the parts are not within a required tolerance, it is possible that the cam-pin 76 be inadvertently dislodged from the push rod 32.

Figure 22:
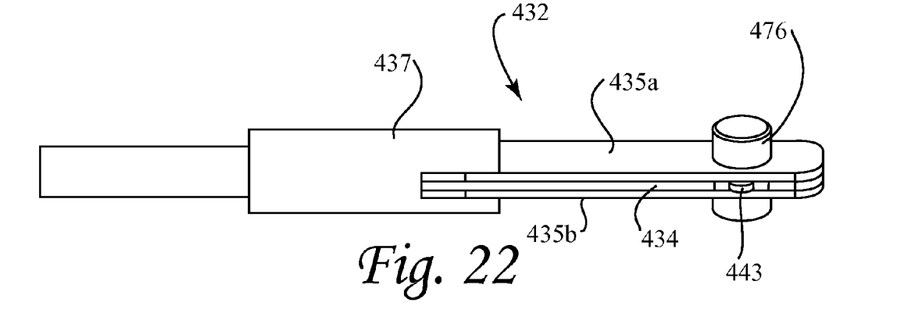
FIG. 22 is a longitudinal perspective view of a second push rod cam-pin assembly for use in the endoscopic instrument.
Figure 23:
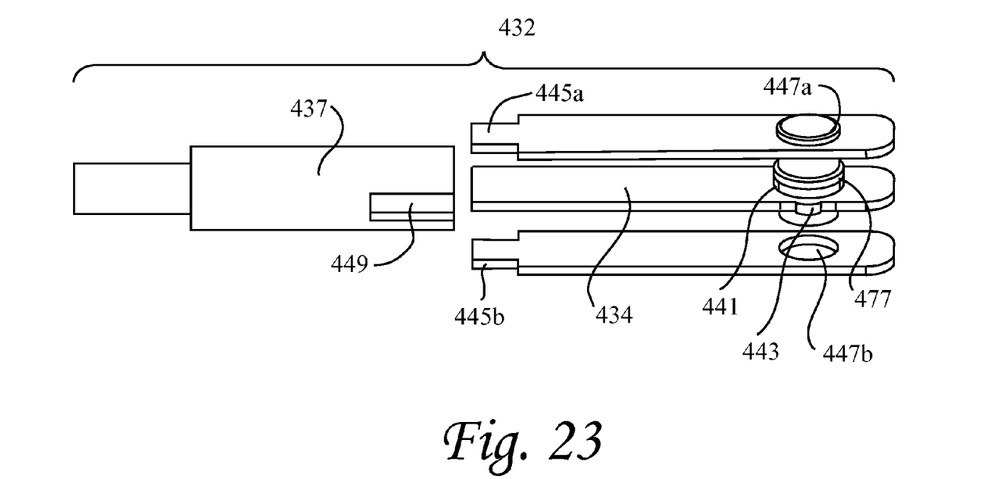
FIG. 23 is an exploded view of the push rod cam-pin assembly shown in FIG. 22.

According to another aspect of the invention, an alternative construction is provided for mating a cam-pin to the push rod that operates open and closing of the end effectors. In a first embodiment of an alternative construction, shown in FIGS. 22 and 23, a cam-pin 476 is machined as a smooth cylinder having a ring boss 477 at least partially and preferably fully extending about its circumference. The push rod 432 is assembled from four parts: a flat plate-like central neck piece 434, two flat plate-like outer neck pieces 435a, 435b positioned one on either side of the central neck piece, and a proximal tubular base 437 which receives the three neck pieces at its distal end. The three neck pieces 434, 435a, 435b are preferably photo-etched (PCM) or stamped into the now described configuration. The central neck piece 434 is an elongate plate having a circular opening 441 extending through the plate at its distal end. The circular opening 441 is sized to closely receive the ring boss 477 of the cam-pin. The thickness of the plate in a dimension extending within the plane of the plate; i.e., at 443, may be increased about portions of the circular opening 441 to maintain structural integrity. The outer neck pieces 435a, 435b are each elongate plates of substantially the same length as the central neck piece and are provided with a proximal reduced width portion 445a, 445b in the dimension through the plane of the plate. The outer neck pieces 435a, 435b each have a circular opening 447a, 447b sized to closely receive the smooth cylindrical portion of the cam-pin 476, but too small in diameter for passage of the ring boss 477. In assembly, the cam-pin 476 is positioned within the central neck piece 434, with the ring boss 477 situated within the opening 441. The outer neck pieces 435a, 435b are then positioned one over each end of the cam-pin 476 so as to retain the ring boss 477 within the opening in the central neck piece 434. The three neck pieces 434, 435a, 435b are then spot welded or otherwise coupled together in a sandwich to create an assembly which effectively holds the cam-pin 476 and from which the cam-pin cannot become loose. The welded assembly is then inserted into an opening 449 at the distal end of the tubular base 437 and laser welded to the tubular base to complete the assembly of the cam-pin to the push rod. This assembly can be automated and permits a greater manufacturing throughput than CNC machining of the parts to the close tolerances required in the conventional assembly.

Figure 24:
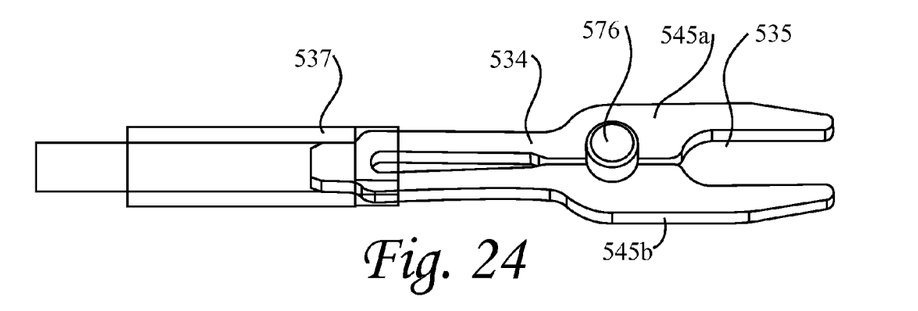
FIG. 24 is a partially transparent longitudinal perspective view of third push rod cam-pin assembly for use in the endoscopic instrument.
Figure 25:
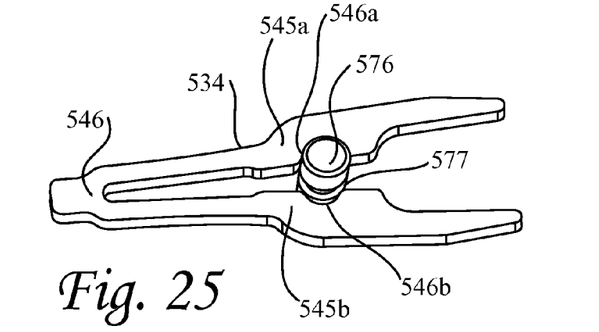
FIG. 25 is an exploded view of a portion of the push-rod cam-pin assembly shown in FIG. 24.
Figure 26:
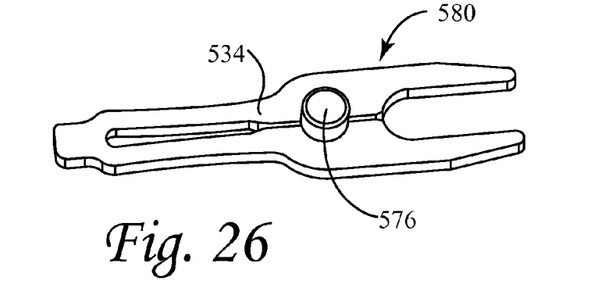
FIG. 26 is a perspective view of the portion of the push-rod cam-pin assembly shown in FIG. 25.

Referring to FIGS. 24 through 26, a second embodiment of a push rod cam-pin assembly is shown which is usable for the embodiments of an end effector shown in FIGS. 3 and 4, as well in FIGS. 11 through 14. The cam-pin 576 defines a mating groove 577. A single machined or stamped plate 534 forms two arms 545a, 545b coupled at a bridge portion 546. The insides of the arms define constant-radiused concave portions 546a, 546b that extend within the mating groove 577 and thus capture the cam-pin 576. The distal ends of the arms preferably, though optionally, form a guiding portion 535 that functions as described above with respect to FIGS. 18 through 20. Referring to FIG. 25, the arms 545a, 545b may be formed in the open configuration (for placement about the cam-pin 576). The arms are then bent closed about the cam-pin and laser welded or otherwise secured together into the subassembly 580 shown in FIG. 26. Alternatively, the arms 545a, 545b may be formed substantially closed, with insufficient space to receive the cam-pin. The arms 545a, 545b are then resiliently bent open to receive the cam-pin 576, and then released to snap back about the cam-pin 576. The arms 545a, 545b are then preferably laser welded or otherwise secured together about the cam-pin. Once the plate 535 has been secured about the cam-pin 576, the proximal end of the plate adjacent the bridge 546 is then fixed to a tubular base 537 to complete the assembly.

Referring to another aspect of the instrument, the end effector assembly 20 is rotatable about the axis of the tubular member 12 by rotation of the control member 28, as actuated from the proximal handle 30. Turning again back to FIG. 4, to facilitate effective and smooth rotation when the control member 28 is subject to a torque at the proximal handle assembly 30, the clevis is mounted to the tubular member with a rotational bearing assembly 80. More particularly, an inner bearing 82 is fixed to the distal end 16 of the tubular member either through bonding, welding or mechanical means such as crimping. The inner bearing 82 includes distal bearing surfaces extending from the distal end of the tubular member. The bearing surfaces include a distal face 84 and a circumferential face 86. The proximal face 88 of the clevis 18 rotatably bears against the distal face 84 of the inner bearing 82. An outer bearing 90 is rotatably mounted on said circumferential face 86 of said inner bearing 82 and is secured about a proximal portion 92 of the clevis 18, e.g., by crimping, to longitudinally secure the clevis in a smoothly rotatable manner to the inner bearing 82 and thus to the tubular member. Torque applied to the control member 28 is thus transferred to the push rod 32 and cam-pin 76 at the distal end thereof to directly rotate the end effectors 22, 24 on the clevis 18 about the distal end of the tubular member 16. Importantly, the torque is applied directly to the end effectors 22, 24, rather than the clevis 18 (from which the control member 28 is de-coupled).

Figure 27:
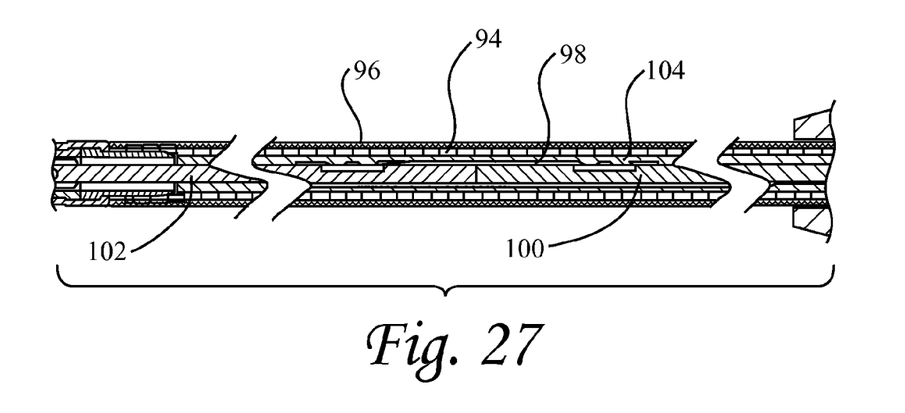
FIG. 27 is a broken section view of a central portion of the endoscopic instrument.

Referring now to FIG. 27, the tubular member 12 is preferably a flat or round wire wound coil 94 defining a flexible construct with a lubricious polymeric flexible outer jacket 96. The control member 28 is constructed to have different torsional and longitudinal stiffness along proximal and distal portions of its length. The control member 28 is preferably constructed of discrete proximal and distal portions that are joined with a coupling element 98, e.g., a short length of hypotube crimped to join such portions. The proximal portion 100 is preferably a single spring steel stainless wire or a flexible composite carbon rod, but could also be made from a bi-radially wound wire cable (wound in opposing directions like "speedometer" cable). The distal portion 102 has a length of 8 to 20 inches, and more preferably approximately 12 inches, and is a thin multi-strand cable of the above type or a drawn brazed strand (DBS) cable; i.e., a cable that has been drawn down in a die and brazed to bind the wires together to reduce the tendency of the cable to unwind if rotated against a load in the opposite direction of the winding. Alternatively, the distal portion is a single superelastic metal wire. The distal portion is capable of offering significant resilient flexibility, as well as accurate and directionally even application of torque—both clockwise and counterclockwise—without causing jump or whip (uneven or sudden rotation). The use of two discrete portions optimizes the control member in cost, function and repeatability. At the proximal portion of the instrument, the instrument remains relatively straight during use and the single steel wire or composite rod 100 is readily adapted to impart the longitudinal displacement and rotational torque from the proximal handle. The distal portion of the instrument can be subject to dramatic distortion as the instrument is bent through the tortuous path of a highly flexed (or even retroflexed) endoscope. A multistrand cable or superelastic wire is well-adapted to effect longitudinal displacement along such portion of the instrument as well as provide accurate and directionally even torque even while the distal end of the instrument is severely bent or retroflexed over. The distal end of the control member 28 is provided with the push rod 32, as discussed above, although other distal structure can be provided for attaching the control member to the end effectors. A polymeric tubular bearing 104 is provided between the control member 28 and the wound wire coil 94 to take up the space between the two elements and prevent buckling of the control member 28.

Referring back to FIGS. 1 and 2, the handle assembly 34 included a shaft 110 having a distal end 111, a proximal thumb ring 112 and a longitudinal slot 114. A ferrule 118 is rotatably mounted to a distal end 111 of the shaft 110 in communication with the longitudinal slot 114. The proximal end of the tubular member 14 is fixed within the ferrule 118. A finger spool 120 is longitudinally displaceable on the shaft 110 at the slot 114. The proximal end 122 of the control member is fixed with the spool 120, e.g., with a set screw 124. Longitudinal displacement of the spool 120 on the shaft causes longitudinal displacement of the control member 28 relative to the tubular member 12 and operation of the end effectors, as discussed above. Rotation of the shaft 110 and spool 120 relative to the ferrule 118 causes rotation of the control member 28 relative to the tubular member 12 and resultant rotation of the end effectors elements 22, 24 relative to the tubular member as also discussed above.

There have been described and illustrated herein embodiments of an endoscopic instrument. While particular embodiments of the invention have been described, it is not intended that the invention be limited thereto, as it is intended that the invention be as broad in scope as the art will allow and that the specification be read likewise. Thus, while the instrument has been described particularly with respect to a scissors device, it will be appreciated that numerous aspects of the device have application in other endoscopic instruments having end effectors other than scissor blades. For example, at least the cam-slot design, end effector rotatable bearing mount, and control member for operating the end effector are concepts applicable to endoscopic instruments in general, including graspers and forceps. In addition, while two exemplar off-set tissue stops have been disclosed with respect to scissor blades, other tissue stop designs in accord with the invention can be provided to the ground surface extension of the cutting edge as well the adjacent surface of the scissor blade opposite the medial surface. It is therefore appreciated by those in the art that yet other modifications could be made to the provided invention without deviating from its spirit and scope as claimed.

What is claimed is:
1. An endoscopic instrument, comprising:
   a) a flexible tubular member having proximal and distal ends, said tubular member sufficiently elastically-flexible to be passed through a tortuous passage of a retroflexed endoscope;

b) a flexible control member having proximal and distal ends and extending through said tubular member;
c) a proximal handle assembly for moving said control member and said tubular member relative to each other;
d) a clevis coupled to said distal end of said tubular member, said clevis defining a longitudinal axis;
e) first and second end effectors rotatably mounted on said clevis at an axle, each end effector including a cam-slot; and
f) an actuation member fixed to said distal end of said control member and extending through said clevis, said actuation member including a cam-pin which rides in at least one of said cam-slots of said end effectors such that longitudinal displacement of said actuation member relative to said clevis moves said end effectors between open and closed configurations, said actuation member is provided with a distal alignment guide located entirely distally of said cam-pin, said distal alignment guide including a longitudinal slot with a flared distal opening and being advanced distally relative to said end effectors to extend about said axle to guide movement of said actuation member relative to said axle and center said actuation member on said axle such that said end effectors open symmetrically about said longitudinal axis.

2. The endoscopic instrument according to claim 1, wherein:
said alignment guide guides movement of said actuation member relative to said axle such that said end effectors open symmetrically even when said actuation member is directed toward said axle in a canted orientation relative to said longitudinal axis of said clevis.

3. The endoscopic instrument according to claim 1, wherein:
said cam-pin extends across said actuation member and into both of said cam-slots of said end effectors.

4. An endoscopic instrument, comprising:
a) a tubular member having proximal and distal ends and defining a longitudinal axis;
b) a clevis coupled to said distal end of said tubular member;
c) first and second end effectors mounted on said clevis, at least one of said end effectors movable relative to the other and including a cam-slot;
d) a control member having proximal and distal ends and extending through said tubular member;
e) an actuation member fixed at said distal end of said control member, said actuation member including a cam-pin that rides within said cam-slot; and
f) a proximal handle assembly coupled to said control member and said tubular member for moving said cam-pin within said cam-slot to move said end effectors between open and closed configurations,
wherein said cam-pin has a central portion which is stepped in diameter relative to surrounding portions of said cam-pin, and said actuation member captures said cam-pin at said central portion of said cam-pin.

5. The endoscopic instrument according to claim 4, wherein:
said central portion of said cam-pin has a larger diameter than said surrounding portions, and
said actuation member comprises three plates including a central plate defining a first diameter hole that receives said central portion of said cam-pin, and two outer plates each having a second diameter hole smaller than said first diameter hole, wherein said central portion of said cam-pin is received in said first diameter hole of said central plate, and said surrounding portions of said cam-pin are received in said second diameter holes of said two outer plates.

6. The endoscopic instrument according to claim 5, wherein:
said three plates are fixed together with a weld.

7. The endoscopic instrument according to claim 5, wherein:
said central portion of said cam-pin has a smaller diameter which defines a groove in said cam-pin, and
said actuation member includes two arm portions having concave portions residing in said groove.

8. The endoscopic instrument according to claim 7, wherein:
said actuation member includes a plate that defines said two arm portions and a bridge portion that connects said two arm portion together.

9. The endoscopic instrument according to claim 4, wherein:
said end effectors are mounted to said clevis with on an axle and said actuation member is provided with a distal alignment guide that extends about said axle when said end effectors are moved to said open configuration to guide movement of said actuation member relative to said axle.

10. The endoscopic instrument according to claim 9, wherein:
said actuation member includes a plate that defines said two arm portions and a bridge portion that connects said two arm portion together, said guide being defined by said arm portions.

* * * * *